(12) United States Patent
Sanai et al.

(10) Patent No.: US 8,097,011 B2
(45) Date of Patent: Jan. 17, 2012

(54) SURGICAL TREATMENT APPARATUS

(75) Inventors: Hideo Sanai, Hachioji (JP); Kenichi Kimura, Hachioji (JP); Masashi Yamada, Sagamihara (JP)

(73) Assignee: Olympus Medical Systems Corp. (JP)

( * ) Notice: Subject to any disclaimer, the term of this patent is extended or adjusted under 35 U.S.C. 154(b) by 292 days.

(21) Appl. No.: 12/037,508

(22) Filed: Feb. 26, 2008

(65) Prior Publication Data

US 2009/0216257 A1 Aug. 27, 2009

(51) Int. Cl.
*A61B 17/32* (2006.01)
(52) U.S. Cl. ........................................ 606/169
(58) Field of Classification Search .............. 606/169, 606/170, 171, 206, 207, 107; 604/22; 601/2; 74/567; 285/81
See application file for complete search history.

(56) References Cited

U.S. PATENT DOCUMENTS

| | | | |
|---|---|---|---|
| 4,867,141 A | 9/1989 | Nakada et al. | |
| 5,466,020 A | 11/1995 | Page et al. | |
| 5,776,155 A | 7/1998 | Beaupre et al. | |
| 6,051,010 A * | 4/2000 | DiMatteo et al. | 606/169 |
| 6,511,098 B1 * | 1/2003 | Luterstein | 285/81 |
| 2002/0107538 A1 * | 8/2002 | Shibata et al. | 606/169 |
| 2007/0060926 A1 * | 3/2007 | Escaf | 606/107 |

FOREIGN PATENT DOCUMENTS

| | | |
|---|---|---|
| DE | 3720424 | 12/1987 |
| EP | 0 893 971 | 4/2004 |
| JP | 2000-506431 | 5/2000 |

OTHER PUBLICATIONS

Search Report issued by the European Patent Office in connection with corresponding application No. EP 09 002 443.1 on Aug. 12, 2009.
Letter from German associate dated Sep. 1, 2009 forwarding the European Search Report dated Aug. 12, 2009 to Japanese associate, including discussion of relevancy thereof.
Japanese Office Action mailed Oct. 4, 2011 in connection with corresponding Japanese Patent Application No. 2009-021676.
English translation of Japanese Office Action issued in connection with corresponding Japanese application provided as an explanation of prior art relevancy.

* cited by examiner

*Primary Examiner* — Ryan Severson
*Assistant Examiner* — Tin Nguyen
(74) *Attorney, Agent, or Firm* — Ostrolenk Faber LLP

(57) ABSTRACT

A surgical treatment apparatus includes a first unit including a first vibration transmission member and a first holding member, a second unit including a second vibration transmission member, a second holding member, and an elastic member provided between the second vibration transmission member and the second holding member, configured to be deformed in accordance with a relative arrangement of the second vibration transmission member and the second holding member with respect to the axial direction to give the second vibration transmission member an elastic force in the axial direction, and an adjustment coupling mechanism to couple the first unit and the second unit with each other, arrange the first vibration transmission member and the second vibration transmission member coaxially, and adjust a relative arrangement of the first holding member and the second holding member.

4 Claims, 6 Drawing Sheets

SURGICAL TREATMENT APPARATUS

BACKGROUND OF THE INVENTION

1. Field of the Invention

The present invention relates to a surgical treatment apparatus to treat a living tissue.

2. Description of the Related Art

A specification in European Patent No. 893971 discloses an ultrasonic treatment apparatus as a surgical treatment apparatus. In the ultrasonic treatment apparatus, a surgical instrument is attachable to/detachable from a handpiece assembly. A horn to expand and transmit ultrasonic vibration is inserted through the handpiece assembly. A transmission rod to transmit the ultrasonic vibration is inserted through a cylindrical housing of the surgical instrument. A distal end portion of the housing has a narrow inside diameter and a step surface formed thereon, a flange is formed on the transmission rod, and an elastic member is interposed between the step surface and the flange. The distal end portion of the handpiece assembly and a proximal end portion of the surgical instrument are coupled with each other, and so a distal end portion of the horn in the handpiece assembly and a proximal end portion of the transmission rod in the surgical instrument are pressed against and coupled with each other. As a method of coupling the handpiece with the surgical instrument, screwing is adopted and besides, there are snap-on coupling and twisting lock fitting.

BRIEF SUMMARY OF THE INVENTION

In an aspect of the present invention, a surgical treatment apparatus includes: a first unit including a first vibration transmission member extended in an axial direction, including an end portion, and to transmit ultrasonic vibration, and a first holding member holding the first vibration transmission member; a second unit including a second vibration transmission member extended in an axial direction, including an end portion, and to transmit the ultrasonic vibration, a second holding member holding the second vibration transmission member movable in the axial direction of the second vibration transmission member, and an elastic member provided between the second vibration transmission member and the second holding member, configured to be deformed in accordance with a relative arrangement of the second vibration transmission member and the second holding member with respect to the axial direction of the second vibration transmission member to give the second vibration transmission member an elastic force in the axial direction; and an adjustment coupling mechanism to couple the first unit and the second unit with each other, arrange the first vibration transmission member and the second vibration transmission member coaxially to abut the end portion of the first vibration transmission member and the end portion of the second vibration transmission member against each other, and adjust a relative arrangement of the first holding member and the second holding member with respect to a coaxial direction to be constant to adjust a deformation amount of the elastic member to be constant.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

An embodiment according to the present invention will now be explained hereinafter with reference to the accompanying drawings.

FIGS. 1 to 5B show an embodiment of the present invention.

A surgical instrument as a surgical treatment apparatus according to this embodiment is an ultrasonic output combined high-frequency surgical instrument for abdominal operations.

Figure 1:
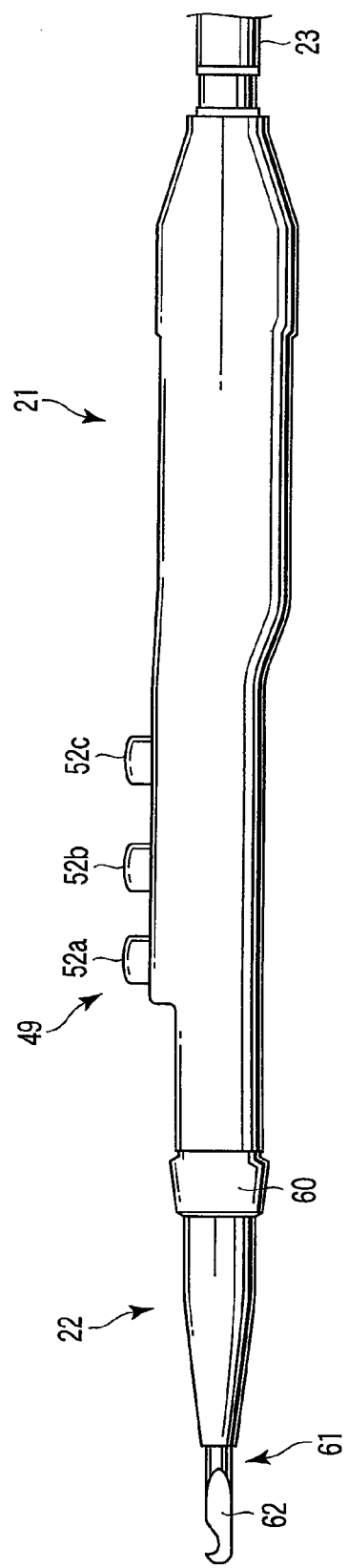
FIG. 1 is a side view showing a surgical instrument according to an embodiment of the present invention.
Figure 2:
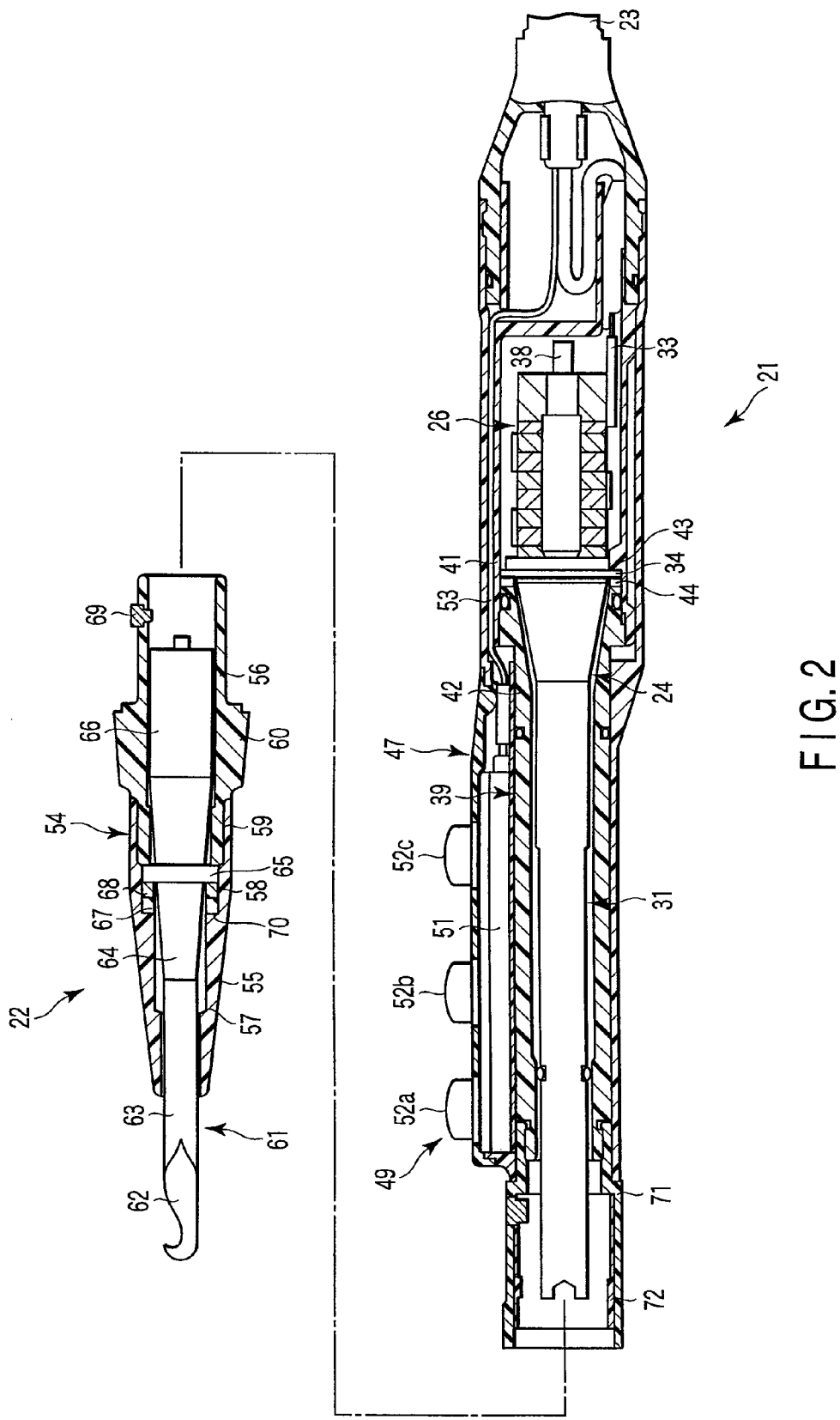
FIG. 2 is a longitudinal cross-sectional view showing the surgical instrument according to the embodiment of the present invention.

An outline structure of the surgical instrument will now be explained with reference to FIGS. 1 and 2.

The surgical instrument includes a handpiece 21 as a first unit to be held and operated by an operator. The handpiece 21 is extended in an axial direction. An electrical cable 23 is extended from a proximal end portion of the handpiece 21, and the electrical cable 23 is connected with a main body.

A vibrator 24 is accommodated in the handpiece 21, and the vibrator 24 is extended in the axial direction of the handpiece 21. A piezoelectric element portion 26 to generate ultrasonic vibration is arranged at a proximal end portion of the vibrator 24, and a horn 31 as a first vibration transmission member to expand and transmit the ultrasonic vibration is arranged on a distal end side of the vibrator 24. Here, a distal end portion of an ultrasonic cable 33 is connected with the piezoelectric element portion 26, and the ultrasonic cable 33 is led to the electrical cable 23. A driving current is supplied from the main body to the piezoelectric element portion 26 through the ultrasonic cable 33, electrical vibration is converted into mechanical vibration in the piezoelectric element portion 26, and the vibrator 24 is ultrasonic-vibrated. Here, an axial length of the vibrator 24 is a length corresponding to one wavelength of the ultrasonic vibration, an axial length of the piezoelectric element portion 26 is a length corresponding to a quarter wavelength of the ultrasonic vibration, and an axial length of the horn 31 is a length corresponding to a three quarter wavelength of the ultrasonic vibration. Further, a proximal end of the horn 31 serves as a node position of the ultrasonic vibration and a flange-like fixing portion 34 is formed on it. A distal end of the horn 31 serves as an antinode position of the ultrasonic vibration. On the other hand, a distal end portion of a high-frequency cable 38 is connected with the piezoelectric element portion 26. The high-frequency cable 38 is led to the electrical cable 23. A high-frequency current is supplied from the main body to the piezoelectric element portion 26 through the high-frequency cable 38 and the high-frequency current flows through the vibrator 24.

The vibrator 24 is accommodated in an inner housing 39 as a first holding member. The inner housing 39 is extended in the axial direction and formed of a proximal-end-side inner cylinder 41 and a distal-end-side inner cylinder 42. The piezoelectric element portion 26 is accommodated in the proximal-end-side inner cylinder 41, and the horn 31 is accommodated in the distal-end-side inner cylinder 41. A protruding portion 43 is extended on a distal-end-side inner peripheral surface of the proximal-end-side inner cylinder 41 in a circumferential direction. A proximal end portion of the distal-end-side inner cylinder 42 is fitted and screwed into a distal end portion of the proximal-end-side inner cylinder 41. The distal-end-side inner cylinder 42 is screwed into the proximal-end-side inner cylinder 41 and so the fixing portion 34 of the vibrator 24 is sandwiched and fixed between the protruding portion 43 of the proximal-end-side inner cylinder 41 and a proximal end surface of the distal-end-side inner cylinder 42. It is to be noted that an annular fixing spacer 44 to adjust the axial fixing position of the vibrator 24 is interposed between a distal end surface of the fixing portion 34 and the proximal end surface of the distal-end-side inner cylinder 42.

The inner housing 39 is accommodated in an outer housing 47. A hand switch portion 49 is arranged on the outer housing 47. In the hand switch portion 49 are arranged an incision output switch 52a, a coagulation output switch 52b, and a simultaneous output switch 52c. A switch cable 53 is extended from a switch main body 51 of the hand switch portion 49, and the switch cable 53 is led to the electrical cable 23. When the incision output switch 52a is pressed, an incision current for high-frequency incision is output from the main body to the piezoelectric element portion 26, thereby driving the surgical instrument in an incision output mode. When the coagulation output switch 52b is pressed, a coagulation current for high-frequency coagulation is output, thereby driving the surgical instrument in a coagulation output mode. When the simultaneous output switch 52c is pressed, a high-frequency current for a high-frequency treatment and a driving current for an ultrasonic treatment are simultaneously output, thereby driving the surgical instrument in a simultaneous output mode.

The surgical instrument includes a sheath unit 22 as a second unit to treat a living tissue. In the sheath unit 22, a probe 61 as a second vibration transmission member is inserted through a cylindrical sheath assembly 54 as a second holding member.

The sheath assembly 54 is formed of a distal-end-side sheath 55 and a proximal-end-side sheath 56. In the distal-end-side sheath 55, a small-inside-diameter portion 57, a medium-inside-diameter portion 58, and a large-inside-diameter portion 59 are sequentially formed from a distal end side toward a proximal end side. A distal end portion of the proximal-end-side sheath 56 is fitted and screwed into the large-inside-diameter portion 59 of the distal-end-side sheath 55. A rotation dial 60 to operate the sheath unit 22 to rotate with respect to the handpiece 21 is formed in a middle portion of the proximal-end-side sheath 56 with respect to the axial direction.

On the other hand, in the probe 61, a treatment portion 62, a small-outside-diameter portion 63, a tapered portion 64, and a large-outside-diameter portion 66 are sequentially formed from a distal end side toward a proximal end side. The treatment portion 62 is used for treating a living tissue and has a non-rotation symmetrical hook-like shape. In the tapered portion 64, an outside diameter is increased from a distal end side toward a proximal end side, and a flange-like pressing portion 65 is formed on this tapered portion 64. Here, an axial length of the probe 61 is a length corresponding to a half wavelength of the ultrasonic vibration, a distal end and proximal end of the probe 61 serve as antinode positions of the ultrasonic vibration, and the pressing portion 65 serves as a node position of the ultrasonic vibration. It is to be noted that an outside diameter of the pressing portion 65 of the probe 61 is equal to or smaller than an outside diameter of the large-outside-diameter portion 66.

The pressing portion 65 of the probe 61 is fitted into the medium-inside-diameter portion 58 of the distal-end-side sheath 55 of the sheath unit 22 such that the pressing portion 65 is slidable in the axial direction but not rotatable around a central axis of the probe 61. That is, with respect to the sheath assembly 54, the probe 61 is movable in the axial direction but not rotatable around the central axis of the probe 61. A step surface between the small-inside-diameter portion 67 and the medium-inside-diameter portion 58 of the distal-end-side sheath 55 forms a support surface 70. An annular elastic member 67 is arranged on the distal end side and an annular pressing spacer 68 is arranged on the proximal end side between the support surface 70 of the distal-end-side sheath 55 and the distal end surface of the pressing portion 65 of the probe 61. The pressing spacer 68 adjusts the compression amount of the elastic member 67. A proximal end surface of the pressing portion 65 of the probe 61 is supported by a distal end surface of the proximal-end-side sheath 56 screwed to the large-inside-diameter portion 59 of the distal-end-side sheath 55. That is, the support surface 70 of the distal-end-side sheath 55 and the distal end surface of the proximal-end-side sheath 56 in the sheath assembly 54 sandwich the elastic member 67, the pressing spacer 68 and the pressing portion 65 of the probe 61 with respect to the axial direction such that the probe 61 is movable in the axial direction with respect to the sheath assembly 54.

Figure 3:
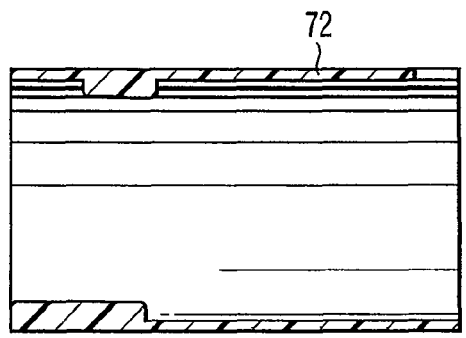
FIG. 3 is a longitudinal cross-sectional view showing a cam frame according to the embodiment of the present invention.
Figure 4:
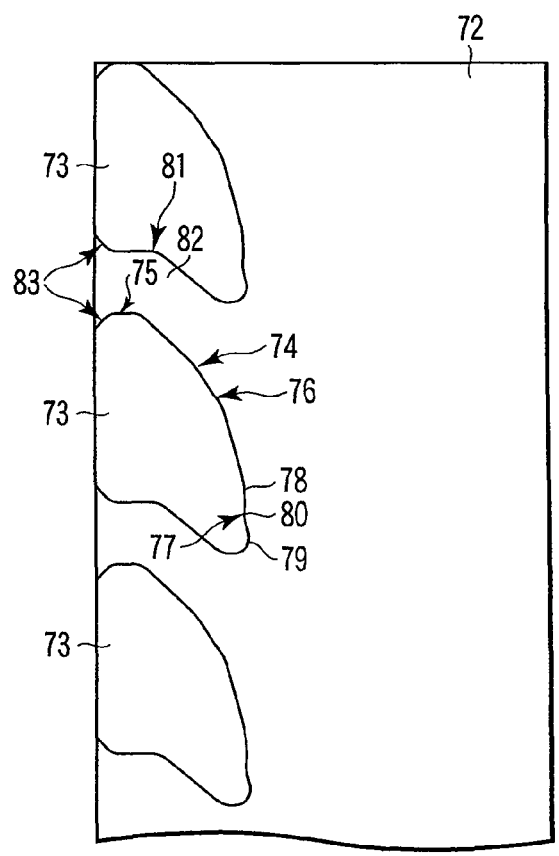
FIG. 4 is a development elevation showing the cam frame according to the embodiment of the present invention.

A cam mechanism to detachably couple the sheath unit 22 and the handpiece 21 with each other will now be explained with reference to FIGS. 2 to 4. Here, the sheath unit 22 and the handpiece 21 are coaxially coupled with each other, and one of circumferential directions for a coaxis is referred to as a coupling direction whilst the other is referred to as a separating direction.

In the sheath unit 22, a cam pin 69 as an actuating portion is protruded in a radial direction toward the outside at the proximal end portion of the proximal-end-side sheath 56. On the other hand, in the hand piece 21, a proximal end of a coupling cylinder 71 is coaxially coupled with the distal end portion of the distal-end-side inner cylinder 42 of the inner housing 39. A cam frame 72 is fitted into and fixed on a distal end side of the coupling cylinder 71. A cam receiving portion 73 convex in the radial direction toward the inside is formed on an inner peripheral surface of the cam frame 72 on a distal end side. A side surface arranged on the separating direction side and facing to the proximal end in side surfaces of the cam receiving portion 73 forms a cam surface 74 as an actuation receiving portion. The cam surface 74 forms an introduction surface 75, an actuation surface 76, and a coupling surface 77 from the distal end side toward the proximal end side. The introduction surface 75 is extended in the axial direction, the actuation surface 76 faces to the separating direction and the proximal end as a whole and is spirally extended around the central axis of the cam frame 72, and the coupling surface 77 faces to the proximal end and is extended in the circumferential direction. Further, a coupling convex surface 78 protruding toward the proximal end is formed at a separating direction end portion of the coupling surface 77, and a rotating convex surface 79 protruding toward the proximal end is formed at a coupling direction end portion of the coupling surface 77. An engaging convex surface 80 serving as a coupling position where the cam pin 69 is engaged is formed between the coupling convex surface 78 and the rotating convex surface 79. Furthermore, four cam receiving portions 73 are arranged at equal intervals with respect to the circumferential direction. A side surface arranged on the coupling direction side and face to the distal end as a whole in side surfaces of the cam receiving portion 73 has a shape that does not obstruct movement of the cam pin 69 along the cam surface 74 of a cam receiving portion adjacent to this cam receiving portion 73 on the coupling direction side, and an introducing groove portion 82 is formed between the cam receiving portions 73 adjacent to each other. It is to be noted that a pair of guide surfaces 83 spreading toward the distal end side in the circumferential direction and to guide the cam pin 69 are formed at distal end portions of both side surfaces of the introducing groove portion 82.

The cam pin 69 of the sheath unit 22 is positioned to the introducing groove portion 82 of the cam frame 72 of the handpiece 21 and the proximal end portion of the sheath unit 22 is inserted in the axial direction into the distal end portion of the handpiece 21, and so the cam pin 69 is moved in the axial direction along the introducing groove portion 82 of the cam frame 72. Here, the probe 61 held by the sheath unit 22 is coaxially arranged with respect to the horn 31 fixed to the handpiece 21, and the proximal end surface of the probe 61 is brought into contact with the distal end surface of the horn 31. The sheath unit 22 is operated to rotate in the coupling direction with respect to the handpiece 21, the cam pin 69 moves along the actuation surface 76 of the cam surface 74, and the sheath assembly 54 of the sheath unit 22 is moved toward the proximal end with respect to the handpiece 21. Here, since the proximal end surface of the probe 61 of the sheath unit 22 is in contact with the distal end surface of the horn 31 of the handpiece 21, the probe 61 cannot move toward the proximal end with respect to the horn 31. Therefore, the sheath assembly 54 is moved toward the proximal end side with respect to the probe 61 in the sheath unit 22, and the elastic member 67 interposed between the probe 61 and the sheath assembly 54 is compressed in the axial direction. The elastic member 67 is compressed in the axial direction, and so a pressing force toward the distal end is applied to the sheath assembly 54 and a pressing force toward the proximal end is given to the probe 61. Due to the pressing force toward the distal end applied to the sheath assembly 54, the cam pin 69 of the sheath assembly 54 is pressed against the cam surface 74 arranged on the distal end side. On the other hand, due to the pressing force toward the proximal end given to the probe 61, a pressing force act between the proximal end surface of the probe 61 and the distal end surface of the horn 31. Further, the sheath unit 22 is operated to rotate in the coupling direction with respect to the handpiece 21, and so the cam pin 69 gets over the coupling convex surface 78 of the cam surface 74 to be engaged with the engaging concave surface 80, thereby coupling the sheath unit 22 with the handpiece 21. When the cam pin 69 gets over the coupling convex surface 78 of the cam surface 74 to be engaged with the engaging concave surface 80, a sense of clicking, e.g., a click sound is produced, it is possible to recognized that the sheath unit 22 and the handpiece 21 are coupled with each other. When separating the sheath unit 22 from the handpiece 21, the sheath unit 22 is operated to rotate in the separating direction with respect to the handpiece 21.

Here, a pressing force amount acting between the proximal end surface of the probe 61 and the distal end surface of the horn 31 corresponds to a pressing force amount given to the probe 61 from the elastic member 67, the pressing force amount of the elastic member 67 is determined corresponding to the compression amount of the elastic member 67, and the compression amount of the elastic member 67 is determined corresponding to a relative axial position of the sheath assembly 54 with respect to the probe 61. Moreover, the relative axial position of the sheath assembly 54 with respect to the probe 61 is determined corresponding to the relative axial position of the sheath assembly 54 with respect to the horn 31. Since the horn 31, the inner housing 39, and the coupling cylinder 71 are integrally fixed in the handpiece 21, the relative axial position of the sheath assembly 54 with respect to the horn 31 is determined corresponding to the relative axial position of the sheath assembly 54 with respect to the coupling cylinder 71. That is, the pressing force amount acting between the proximal end surface of the probe 61 and the distal end surface of the horn 31 is determined corresponding to the relative axial position of the sheath assembly 54 with respect to the coupling cylinder 71. When the sheath unit 22 is coupled with the handpiece 21, the relative axial position of the sheath assembly 54 with respect to the coupling cylinder 71 can be very accurately determined by appropriately setting the axial position of the coupling surface 77 of the cam surface 74, i.e., the axial position of a bottom surface of the engaging concave surface 80 of the cam surface 74. Therefore, the pressing force amount acting between the proximal end surface of the probe 61 and the distal end surface of the horn 31 can be very accurately determined.

Figure 5A:
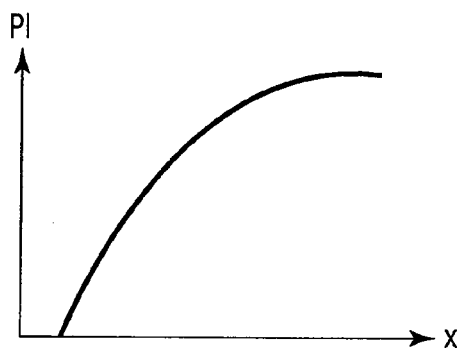
FIG. 5A is a graph showing a relationship between a compression amount and a pressing force amount of an elastic member according to the embodiment of the present invention.
Figure 5B:
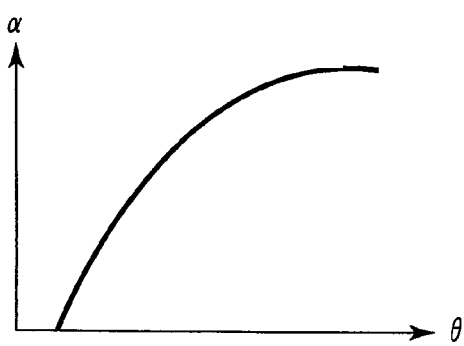
FIG. 5B is a graph showing a relationship between a rotation angle and a pressure angle of a cam mechanism according to the embodiment of the present invention.

Additionally, a rotating operation force amount required to operate the sheath unit 22 to rotate with respect to the handpiece 21 in the coupling direction against the pressing force amount of the elastic member 67 is fixed. That is, as shown in FIG. 5A, a pressing force amount $P_l$ of the elastic member 67 is increased with respect to an increase in the compression amount x of the elastic member 67. A value obtained by multiplying an axial movement amount $\delta 1$ of the sheath assembly 54 with respect to the coupling cylinder 71 by the pressing force amount $P_l$ of the elastic member 67 corresponds to a value obtained by multiplying a rotation angle amount be of the cam mechanism by a rotating operation force amount $P_\theta$. That is, $P_l(x)*\delta 1 \propto P_\theta*\delta\theta$ is achieved. Here, If a pressure angle α of the actuation surface 76 of the cam surface 74 is fixed with respect to a rotation angle θ of the cam mechanism, the axial movement amount $\delta 1$ of the sheath assembly 54 with respect to the rotation angle amount $\delta\theta$ of the cam mechanism, i.e., $\delta 1/\delta\theta$ is fixed. In this case, when the rotation angle θ of the cam mechanism is increased, the compression amount x of the elastic member 67 is increased and the pressing force amount $P_l(x)$ is increased, the necessary rotating operation force amount $P_\theta \propto P_l(x)*(\delta 1/\delta\theta)$ is increased. On the other hand, in this embodiment, as shown in FIG. 5B, the pressure angle α of the actuation surface 76 of the cam surface 74 is appropriately increased with respect to a rise in the rotation angle θ of the cam mechanism, and the axial movement amount $\delta 1$ of the sheath assembly 54 with respect to the rotation angle amount $\delta\theta$ of the cam mechanism, i.e., $\delta 1/\delta\theta$ is appropriately reduced, thereby fixing the rotating operation force amount $P_\theta \propto P_1(x)*(\delta 1/\delta\theta)$.

In the cam mechanism, the four engaging concave surfaces 80 as coupling positions where the cam pin 69 is engaged are arranged at equal intervals with respect to the circumferential direction, and the sheath unit 22 can be coupled with the handpiece 21 in four relative rotation arrangements. When inserting the proximal end portion of the sheath unit 22 into the distal end portion of the handpiece 21 in the axial direction, the introducing groove portion 82 into which the cam pin 69 is to be inserted is selected from the four introducing groove portions 82, and so the relative rotation arrangement of the sheath unit 22 with respect to the handpiece 21 is selected from the four relative rotation arrangements. Furthermore, when the handpiece 21 is being coupled with the sheath unit 22 and the sheath unit 22 is operated to rotate with respect to the handpiece 21 in the coupling direction, the cam pin 69 gets over the rotating convex surface 79 and moves from the engagement concave surface 80. Since the cam pin 69 is pressed toward the distal end due to the function of the elastic member 67, the cam pin 69 is separated from the cam surface 74 against which the cam pin 69 has been pressed, moved toward the distal end, and shifted to the cam surface 74 of the cam receiving portion 73 adjacent to the former cam receiving portion 73 on the coupling direction side. When the sheath unit 22 is operated to further rotate with respect to the handpiece 21 in the coupling direction, the cam pin 69 is moved along the cam surface 74 to which the cam pin 69 has been shifted to be again engaged with the engaging concave surface 80, thereby coupling the sheath unit 22 with the handpiece 21. In this manner, when the sheath unit 22 is being coupled with the handpiece 21, the sheath unit 22 is movable with respect to the handpiece 21 between the four relative rotation arrangements through operating the sheath unit 22 to rotate with respect to the handpiece 21 in the coupling direction. Therefore, the treatment portion 62 of the probe 61 can be arranged with respect to the hand switch portion 49 of the handpiece 21 in an arbitrary direction.

Therefore, the surgical instrument according to this embodiment demonstrates the following effects.

In the surgical instrument according to this embodiment, when coupling the handpiece 21 with the sheath unit 22, the elastic force given to the probe 61 from the elastic member 67 is adjusted to be constant and the pressing force amount acting between the horn 31 and the probe 61 is adjusted to be constant through adjusting the deformation amount of the elastic member 67 to be constant. In particular, using the cam mechanism to couple the handpiece 21 with the sheath unit 22 enables very accurately adjusting the pressing force amount. Here, when the pressing force amount is lower than an appropriate range, ultrasonic vibration cannot be normally transmitted from the horn 31 to the probe 61. On the other hand, when the pressing force amount is higher than the appropriate range, a dynamic impedance is increased, a resistance of the vibrator 24 rises, and a vibration efficiency is reduced. Furthermore, a rotating operation force amount required to operate the sheath unit 22 to rotate with respect to the handpiece 21 against the pressing force amount of the elastic member 67 is increased, thereby making it difficult to perform the rotating operation. In this embodiment, since the pressing force amount is adjusted to fall within the appropriate range, the horn 31 and the probe 61 can be appropriately ultrasonic-vibrated, and the rotating operation is facilitated.

Moreover, the rotating operation force amount is fixed irrespective of the deformation amount of the elastic member 67 in the rotating operation for the handpiece 21 and the sheath unit 22 through changing the pressure angle with respect to the rotation angle in the cam mechanism. Therefore, the rotating operation can be smoothly effected.

Additionally, since the cam pin 69 gets over the coupling convex surface 78 to be engaged with the engaging concave surface 80 and a sense of clicking is produced at the time of engagement with the engaging concave surface 80, it is possible to recognize that the sheath unit 22 and the handpiece 21 is coupled with each other.

Further, the cam pin 69 can be engaged with a desired engaging concave surface 80 in the four engaging concave surfaces 80 arranged at different positions with respect to the circumferential direction, and the sheath unit 22 can be coupled with the handpiece 21 in a desired relative rotation arrangement in the four relative rotation arrangements. Therefore, the surgical instrument can have a conformation suitable for an immediate surgical treatment. In particular, since how to hold the handpiece 21 is appropriately determined in accordance with an arrangement of the hand switch portion 49 in the handpiece 21, in a case where the treatment portion 62 of the probe 61 has a non-rotation symmetrical shape like this embodiment, using the surgical instrument is difficult if the sheath unit 22 cannot rotate with respect to the handpiece 21 and the direction of the treatment portion 62 cannot be changed, but such a situation is avoided in this embodiment.

Moreover, the tapered portion 64 and the small-outside-diameter portion 63 each having a diameter smaller than that of the large-outside-diameter portion 66 is formed in the probe 61 and the flange-like pressing portion 65 is formed on the tapered portion 64, and so the outside diameter of the pressing portion 65 is equal to or smaller than the outside diameter of the large-outside-diameter portion 66. That is, the sheath unit 22 is prevented from having a large diameter, and a reduction in operability of the surgical instrument is avoided. In particular, in the relatively short surgical instrument for abdominal operations like this embodiment, if diameter of the surgical instrument is increased, it is hard to visually recognize the treatment portion 62 at the distal end portion of the surgical instrument and the operability of the surgical instrument is lowered, but such a situation is avoided in this embodiment.

It is to be noted that the treatment portion having the non-rotation symmetrical shape is used in this embodiment, but the present invention can be likewise applied to a treatment portion having a rotation symmetrical shape, for example, a treatment portion wherein a distal end of the prove has a spherical shape.

Additionally, the present invention can be also applied to various surgical treatment apparatuses other than the ultrasonic output combined high-frequency surgical instrument for abdominal operations.

Figure 6:
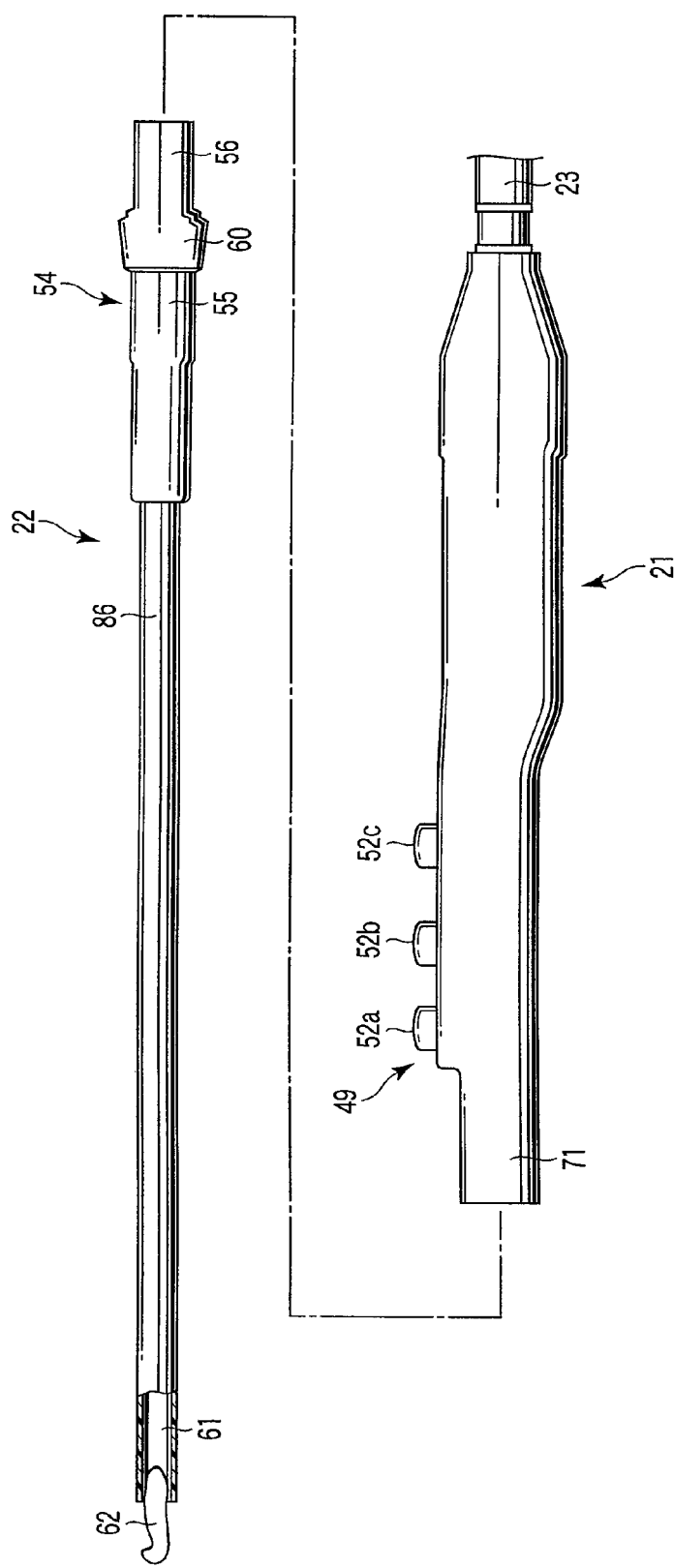
FIG. 6 is a partial longitudinal cross-sectional side view showing a surgical instrument according to a first modification of the embodiment of the present invention.

For example, the present invention can be likewise applied to such an ultrasonic output combined high-frequency surgical instrument for endoscopic operations as shown in FIG. 6. In the surgical instrument depicted in FIG. 6, a handpiece 21 and a sheath unit 22 having the same structures as those in the foregoing embodiment are used. However, the sheath unit 22 is long, and a proximal end portion of an insertion sheath 86 is fitted into and fixed on a distal end portion of a distal-end-side sheath 55, and a probe 61 is inserted through the insertion sheath 86. An axial length of the probe 61 is a length corresponding to an integral multiple of a half wavelength of ultrasonic vibration.

Figure 7:
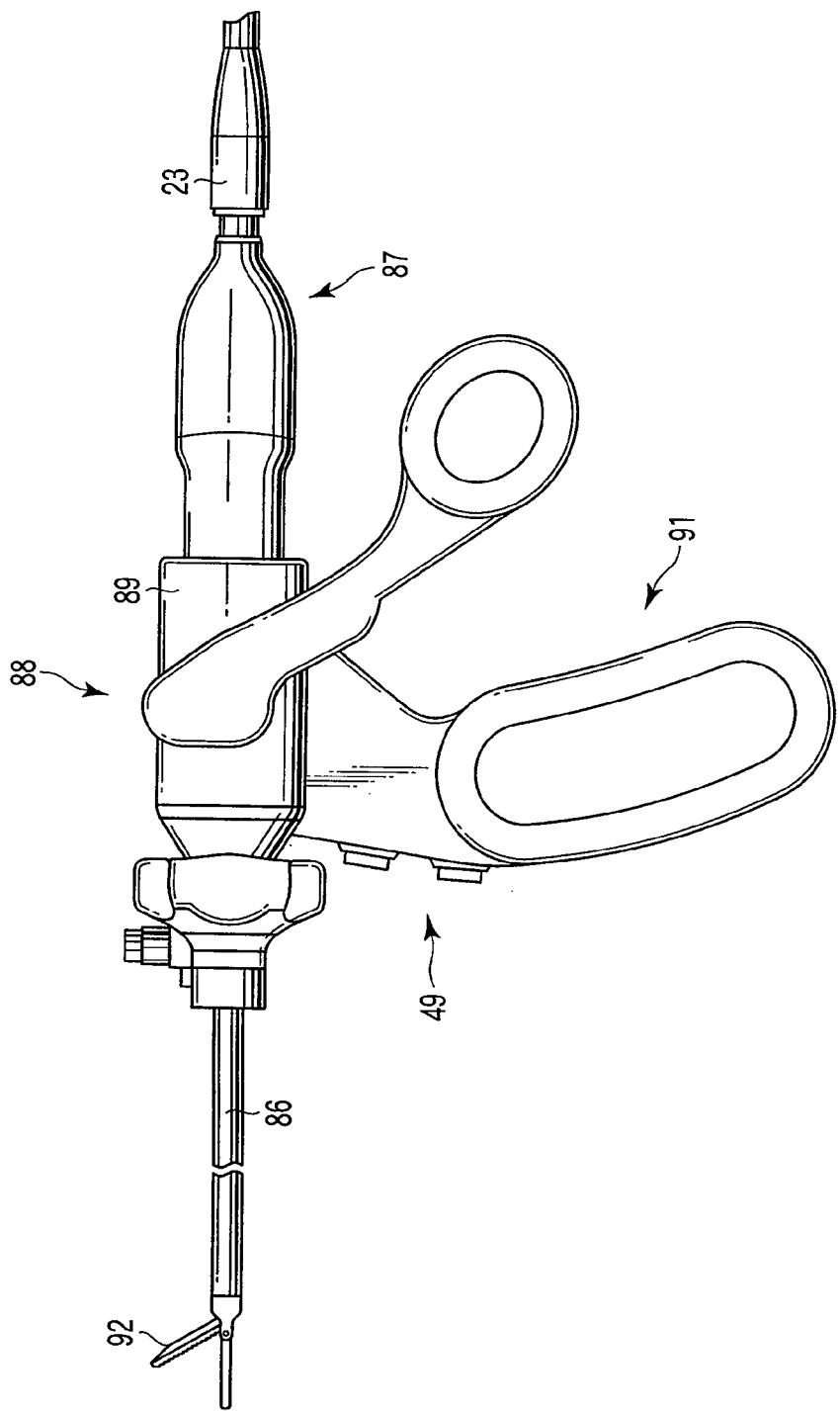
FIG. 7 is a side view showing a surgical instrument according to a second modification of the embodiment of the present invention.

Further, for example, the present invention can be also applied to such an ultrasonic surgical instrument for endoscopic operations as shown in FIG. 7. In the surgical instrument depicted in FIG. 7, a probe 61 is inserted through an insertion sheath 86 of a sheath unit 22. A jaw 92 is pivotally attached to a distal end portion of the insertion sheath 86, and the jaw 92 is opened/closed with respect to a treatment portion 62 at a distal end portion of the probe 61 such that it can grasp a living tissue in cooperation with the probe 61. A proximal end portion of the sheath unit 22 is coupled with a distal end side of a handle unit 88. A pair of handles 91 is protruded from a cylindrical main body portion 89 of the handle unit 88, and the jaw 92 is opened/closed through opening/closing the pair of handles 91. Further, a hand switch portion 49 is arranged at the handle 91 on the distal end side. A distal end portion of a vibrator unit 87 is detachably coupled with a proximal end side of the main body portion 89 of the handle unit 88. Here, the vibrator unit 87 has the same structure as the handpiece 21 in the foregoing embodiment. However, in this modification, the hand switch portion 49 is arranged on the handle unit 88 rather than the vibrator unit 87, the handle unit 88 is connected with the vibrator unit 87 through an appropriate electrical connection mechanism, and the hand switch portion 49 is connected with a main body. Furthermore, the same cam pin as that in the foregoing embodiment is arranged at a distal end portion of the vibrator unit 87, and a cam frame is arranged in the main body portion 89 of the handle unit 88. Moreover, when the vibrator unit 87 is coupled with the handle unit 88 by using a cam mechanism, the proximal end portion of the probe 61 is pressed against the distal end portion of the horn 31 to be coupled with each other in the main body portion 89 of the handle unit 88.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A surgical treatment apparatus comprising:
a first unit including a first vibration transmission member extended in an axial direction, including an end portion, and configured to transmit ultrasonic vibration, and a first holding member holding the first vibration transmission member;
a second unit including a second vibration transmission member extended in an axial direction, including an end portion, and configured to transmit the ultrasonic vibration, a second holding member holding the second vibration transmission member movable in the axial direction of the second vibration transmission member, and an elastic member provided between the second vibration transmission member and the second holding member, configured to be deformed in accordance with a relative arrangement of the second vibration transmission member and the second holding member with respect to the axial direction of the second vibration transmission member to give the second vibration transmission member an elastic force in the axial direction; and
a cam mechanism including an actuating receiving portion provided to one of the first holding member and the second holding member, spirally extended around the axial direction, and including a coupling position, and an actuating portion provided to other of the first holding member and the second holding member and configured to be moved along the actuation receiving portion and arranged at the coupling position to couple the first unit and the second unit with each other, arrange the first vibration transmission member and the second vibration transmission member coaxially to abut the end portion of the first vibration transmission member and the end portion of the second vibration transmission member against each other, and adjust a relative arrangement of the first holding member and the second holding member with respect to a coaxial direction to be constant to adjust a deformation amount of the elastic member to be constant, and
wherein the cam mechanism changes a pressure angle with respect to a rotation angle such that a rotating operation force amount is fixed in a rotating operation of relatively moving the first holding member and the second holding member in the coaxial direction against the elastic force of the elastic member.

2. The surgical treatment apparatus according to claim 1, wherein the cam mechanism includes an irregular shape that is convex and concave in a direction crossing the actuation receiving portion in front of the coupling position in the actuation receiving portion.

3. The surgical treatment apparatus according to claim 1, wherein the cam mechanism includes first and second coupling positions arranged at different positions with respect to a circumferential direction.

4. The surgical treatment apparatus according to claim 1, wherein the second vibration transmission member includes a large-outside-diameter portion formed on one end side with respect to the axial direction in the second vibration transmission member, a small-outside-diameter portion formed on the other end side with respect to the axial direction in the second vibration transmission member and having a smaller outside diameter than that of the large-outside-diameter portion, a tapered portion formed between the large-outside-diameter portion and the small-outside-diameter portion in the second vibration transmission member and having an outside diameter reduced from the one end side toward the other end side in the axial direction, and a pressing portion provided on the tapered portion or the smaller-outside-diameter portion and protruded in a radial direction, and the elastic member is provided between the pressing portion and the second holding member with respect to the axial direction.

* * * * *